United States Patent
Stanke

(10) Patent No.: US 6,510,395 B2
(45) Date of Patent: Jan. 21, 2003

(54) METHOD OF DETECTING RESIDUE ON A POLISHED WAFER

(75) Inventor: Fred E. Stanke, Cupertino, CA (US)

(73) Assignee: Sensys Instruments Corporation, Santa Clara, CA (US)

( * ) Notice: Subject to any disclaimer, the term of this patent is extended or adjusted under 35 U.S.C. 154(b) by 47 days.

(21) Appl. No.: 09/800,306

(22) Filed: Mar. 1, 2001

(65) Prior Publication Data

US 2002/0022936 A1 Feb. 21, 2002

Related U.S. Application Data

(60) Provisional application No. 60/224,827, filed on Aug. 11, 2000.

(51) Int. Cl.$^7$ .............................................. G06F 19/00
(52) U.S. Cl. .............................................. 702/81; 702/1
(58) Field of Search .................. 348/370; 356/118, 356/239.8, 369, 381, 382; 371/22.1; 438/14; 700/121; 702/34, 35, 71, 76, 77, 81, 82, 83, 84, 1

(56) References Cited

U.S. PATENT DOCUMENTS

| | | | |
|---|---|---|---|
| 4,053,232 A | 10/1977 | Dill et al. | 356/118 |
| 4,999,014 A | 3/1991 | Gold et al. | 356/382 |
| 5,166,752 A | 11/1992 | Spanier et al. | 356/369 |
| 5,539,752 A * | 7/1996 | Berezin et al. | 371/22.1 |
| 5,910,846 A | 6/1999 | Sandhu | 356/381 |
| 5,991,699 A * | 11/1999 | Kulkarni et al. | 702/83 |
| 6,108,091 A * | 8/2000 | Pecen et al. | 356/381 |
| 6,169,601 B1 * | 1/2001 | Eremin et al. | 356/239.8 |
| 6,195,127 B1 * | 2/2001 | Sugimoto | 348/370 |
| 6,274,394 B1 * | 8/2001 | Cha | 438/14 |
| 6,289,257 B1 * | 9/2001 | Sekine | 700/121 |
| 6,303,394 B1 * | 10/2001 | Steffan et al. | 438/14 |
| 6,377,898 B1 * | 4/2002 | Steffan et al. | 702/82 |

FOREIGN PATENT DOCUMENTS

WO    WO 00/54935    9/2000

OTHER PUBLICATIONS

M.E. Lee et al., "Analysis of Reflectometry and Ellipsometry Data From Patterned Structures", Int'l Conference on Characterization and Metrology for ULSI Technology, Mar. 23–27, 1998, AIP Conference Proceedings 449, pp. 331–335 (1998).

The Book *The Fourier Transform and Its Applications* by Bracewell.

The Book *Image Analysis and Mathematical Morphology* by J. Serra.

* cited by examiner

*Primary Examiner*—John S. Hilten
*Assistant Examiner*—Douglas N Washburn
(74) *Attorney, Agent, or Firm*—Thomas Schneck; Mark Protsik

(57) ABSTRACT

An apparatus for and method of determining the states on a wafer to be processed, e.g., whether residue in the form of metal is left on the surface of a wafer after chemical-mechanical polishing. The method comprises the steps of calculating first spectral signatures from a first set of measurement sites on one or more training wafers. Each measurement site is known to be in one of two or more states. In the case of only two states, the states could be "residue present" and "residue absent" states. The next step involves correlating the first spectral signatures to the states on the training wafer(s). The next step then involves calculating second spectral signatures from a second set of measurement sites on a wafer where the states are unknown. The final step is determining the states on the wafer to be processed based on the second spectral signatures.

24 Claims, 12 Drawing Sheets

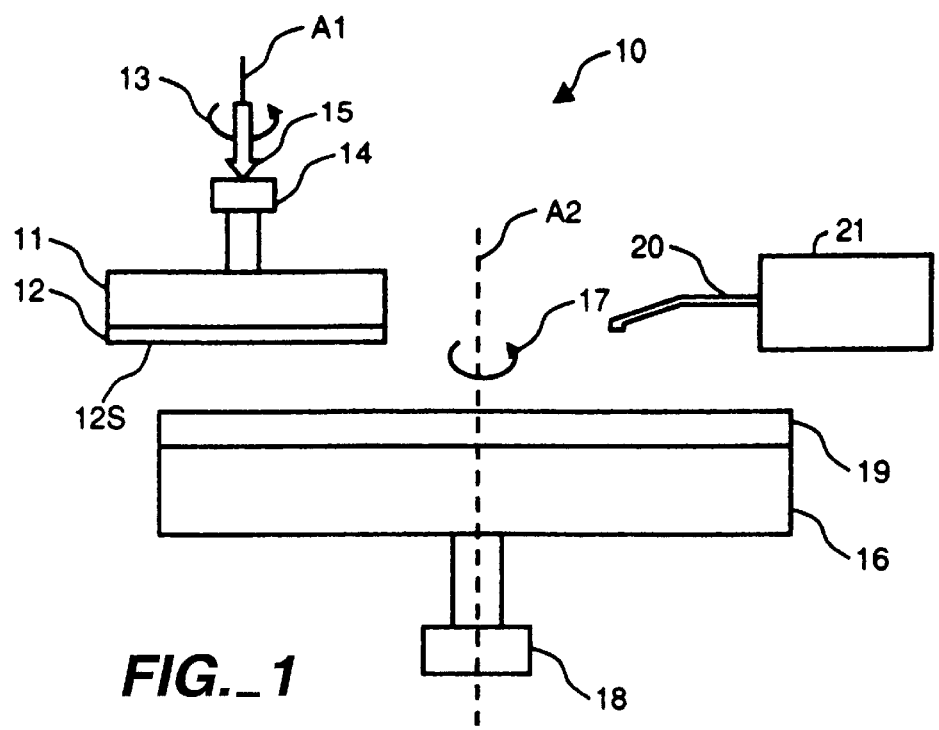
*FIG._1*
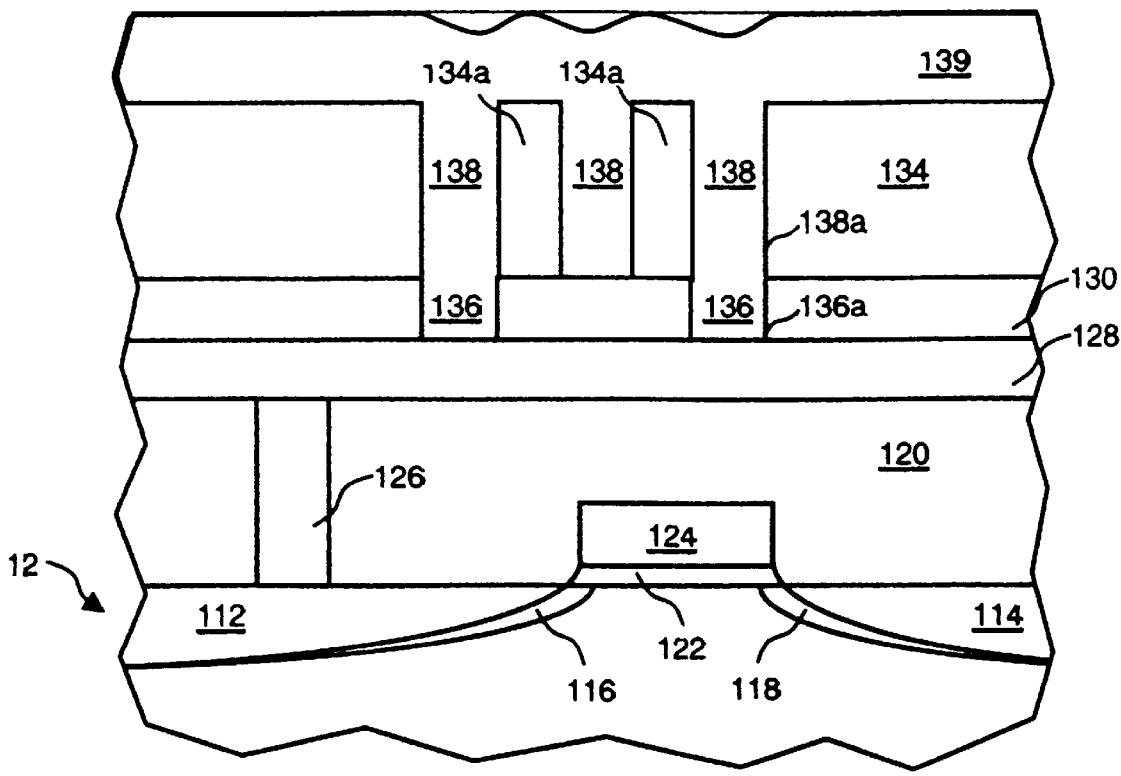
*FIG._2*

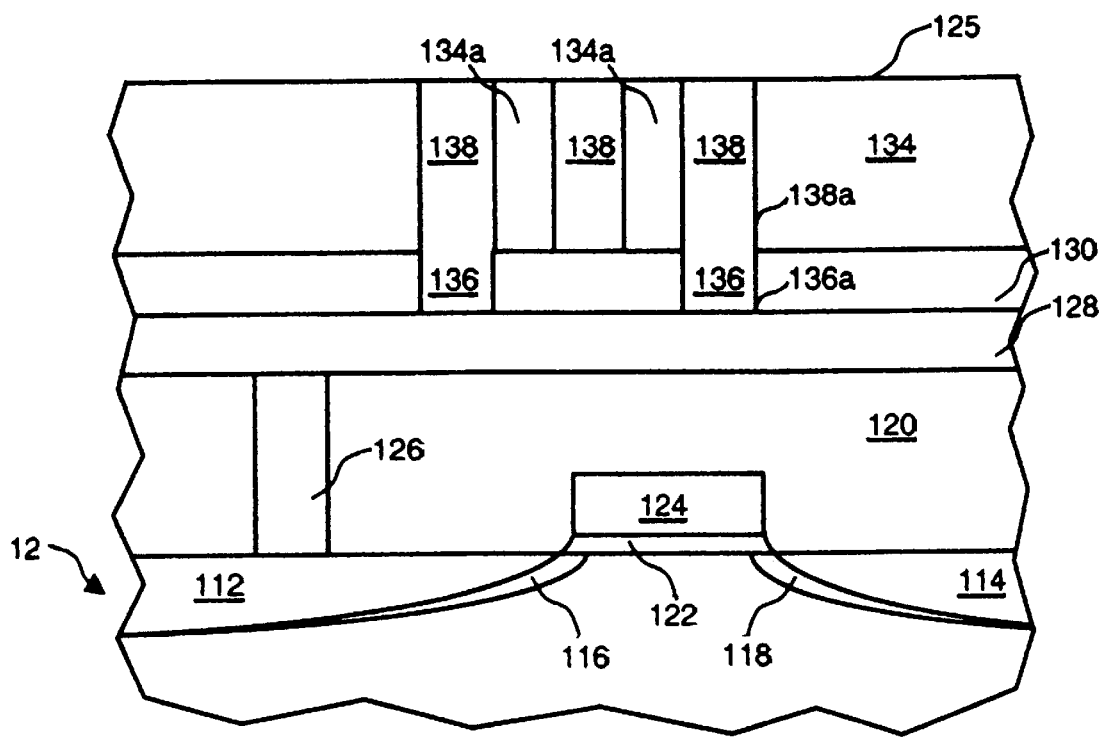
FIG._3A
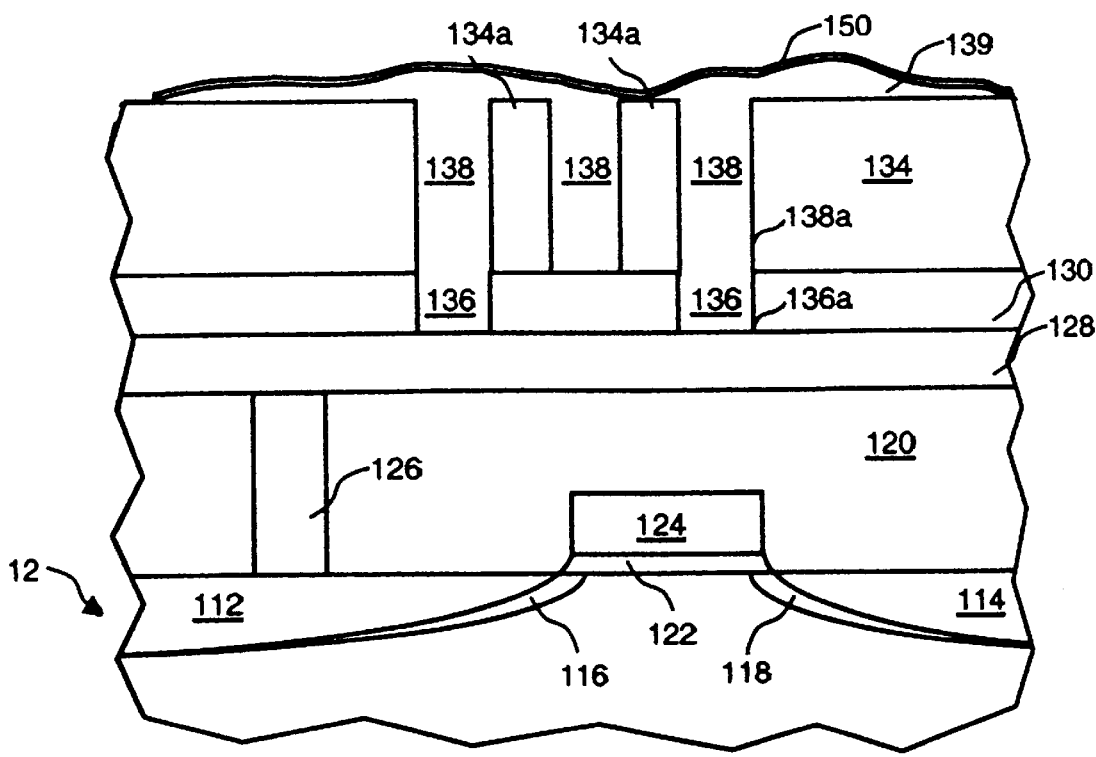
FIG._3B

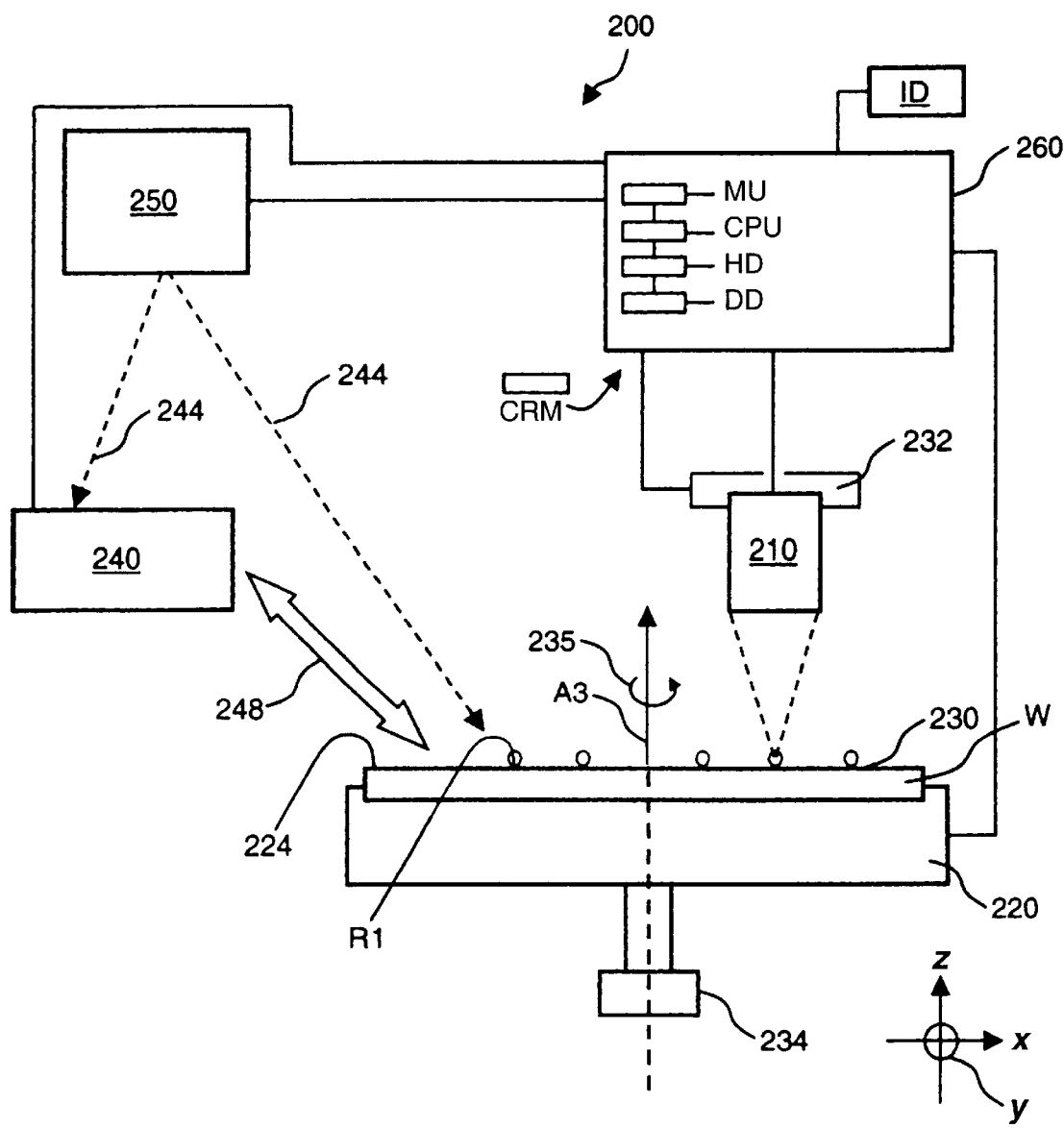
FIG._4

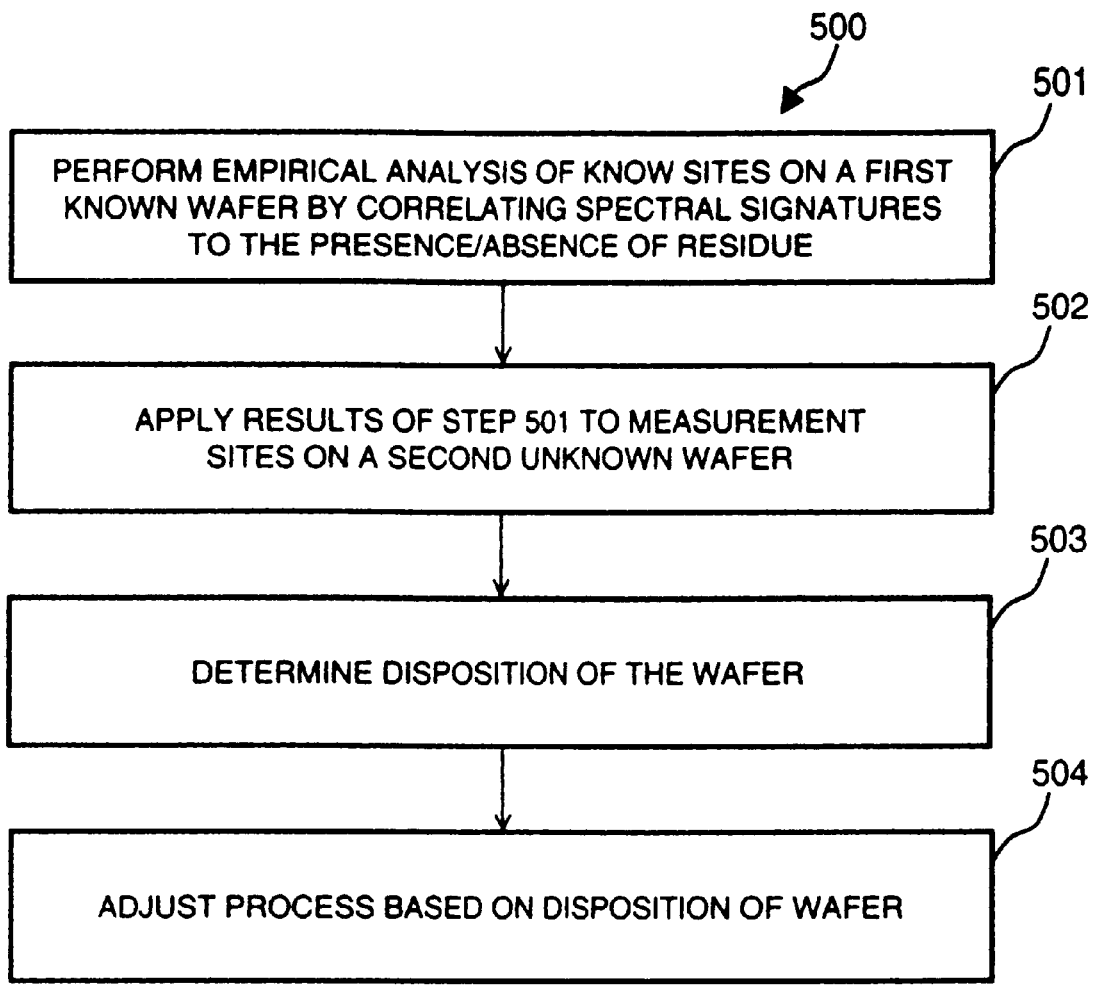
FIG._5

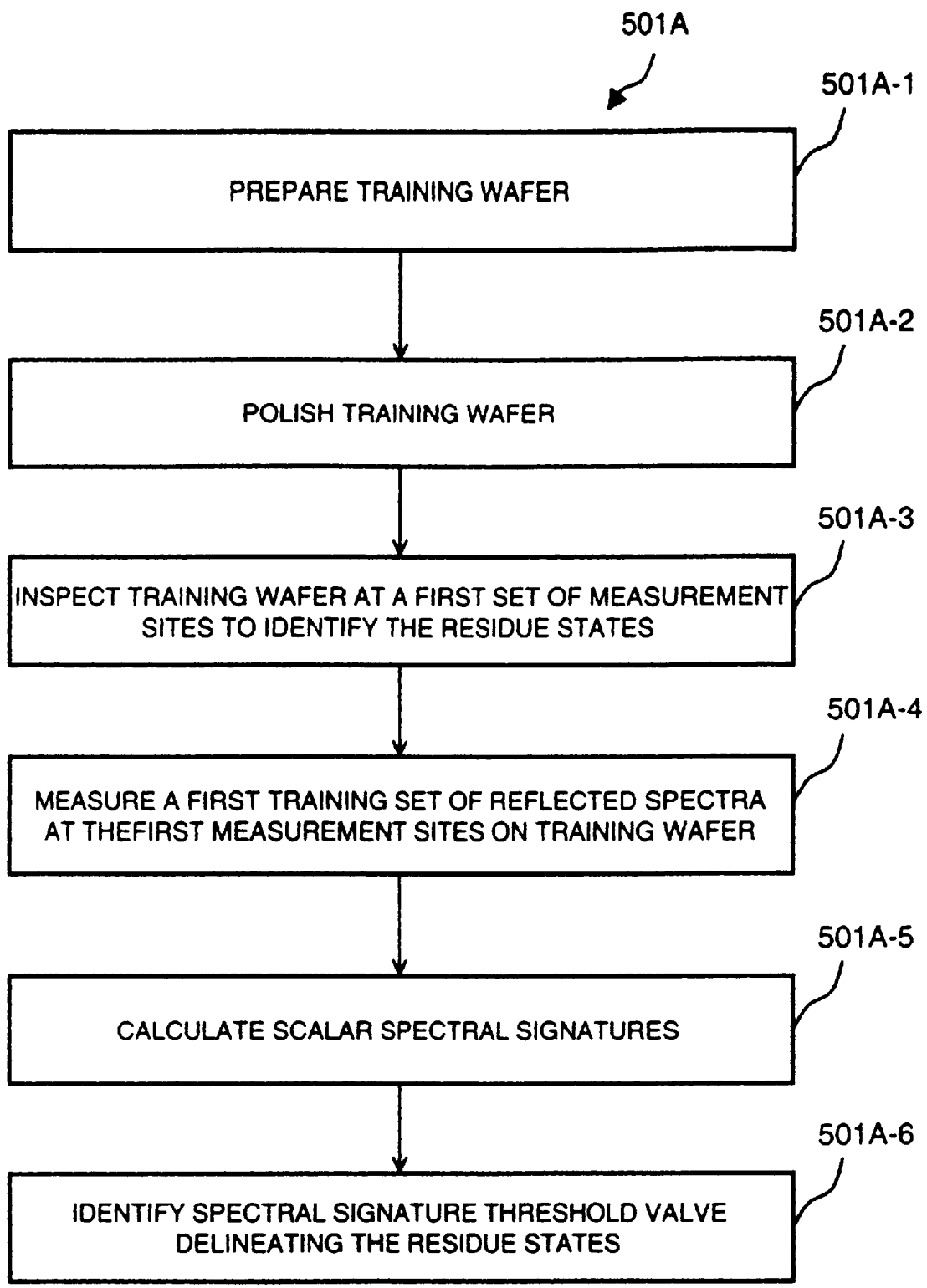
FIG._6

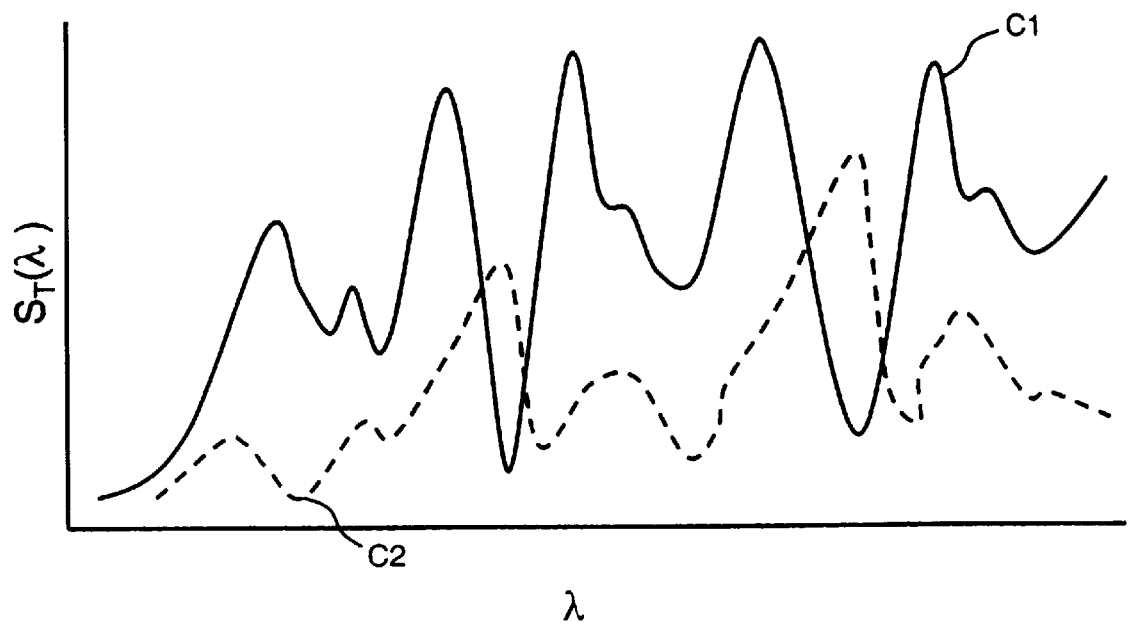
FIG._7
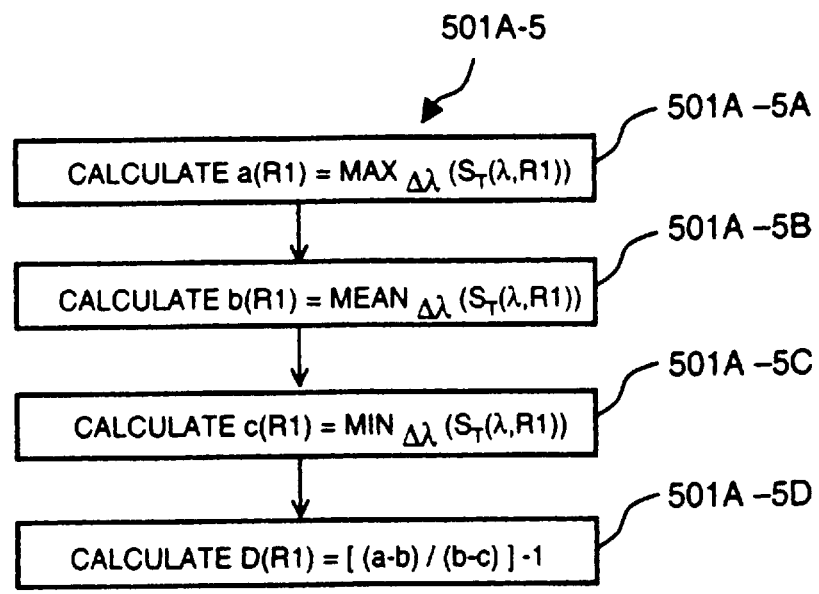
FIG._8

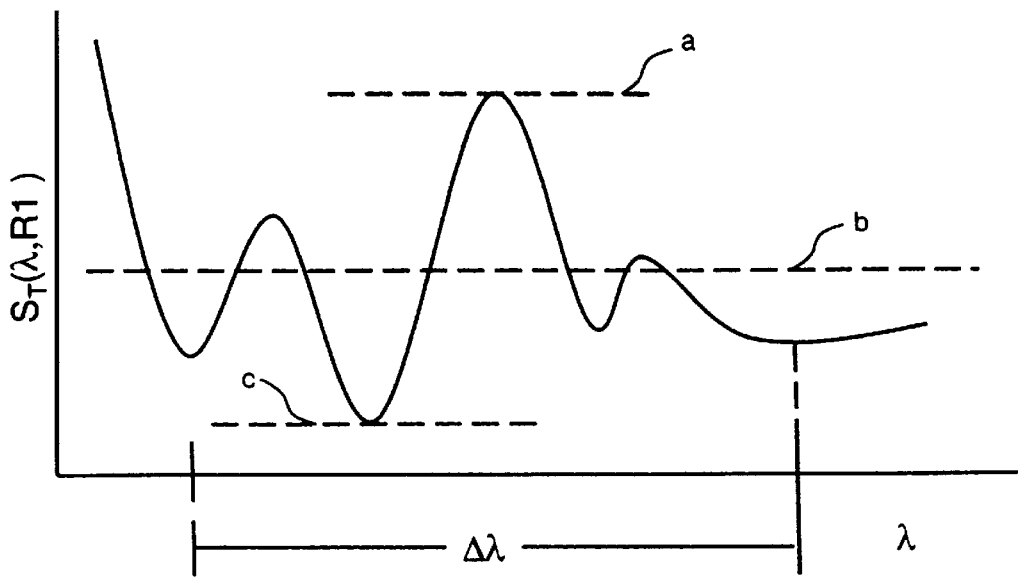
FIG._9
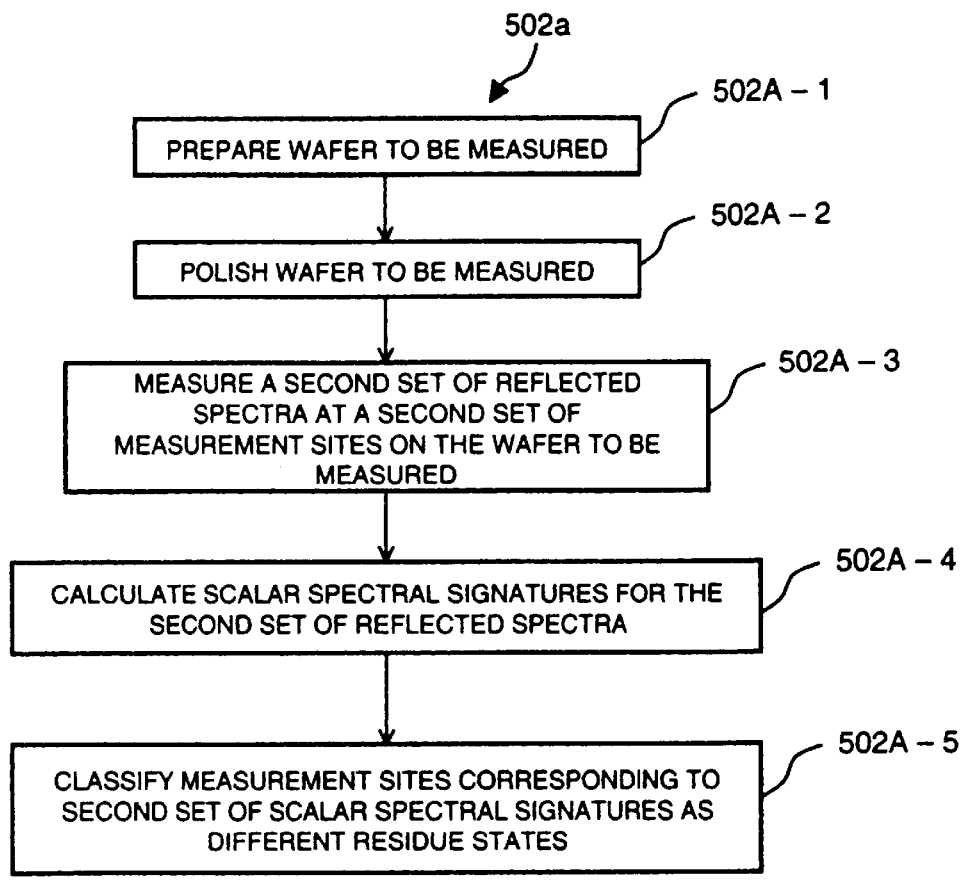
FIG._10

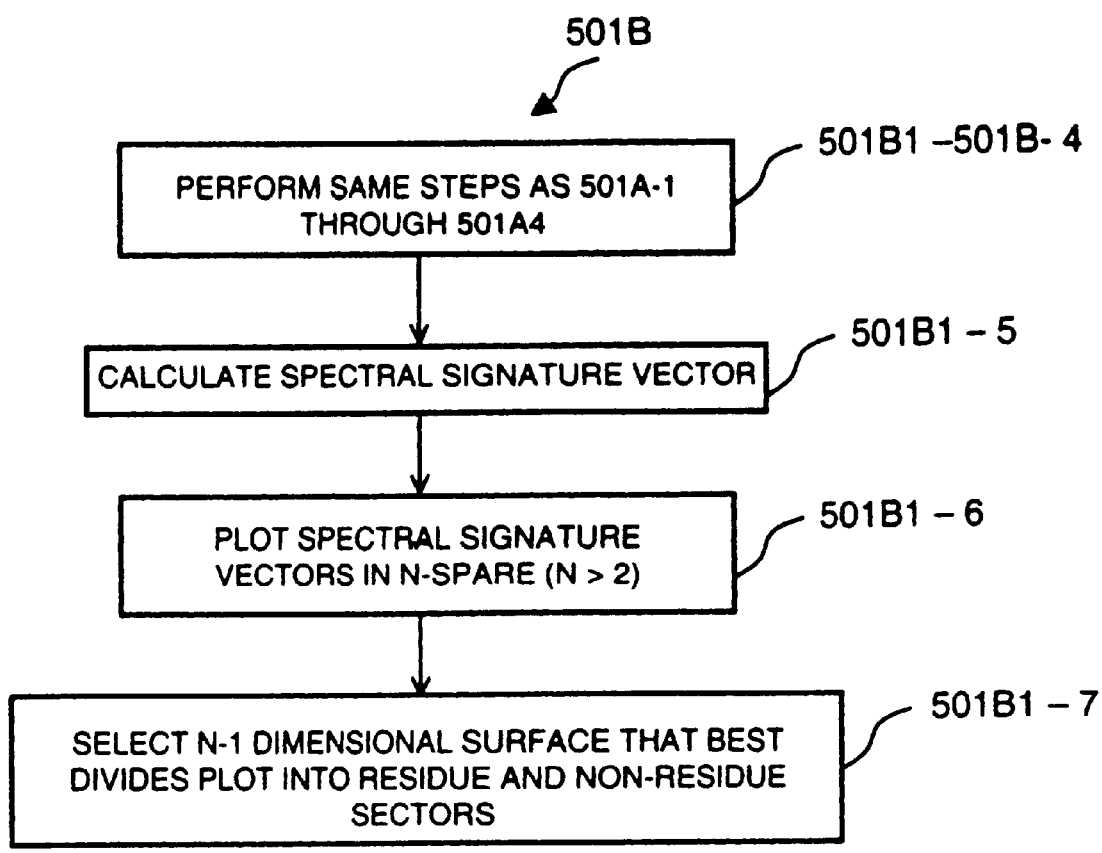
FIG._11

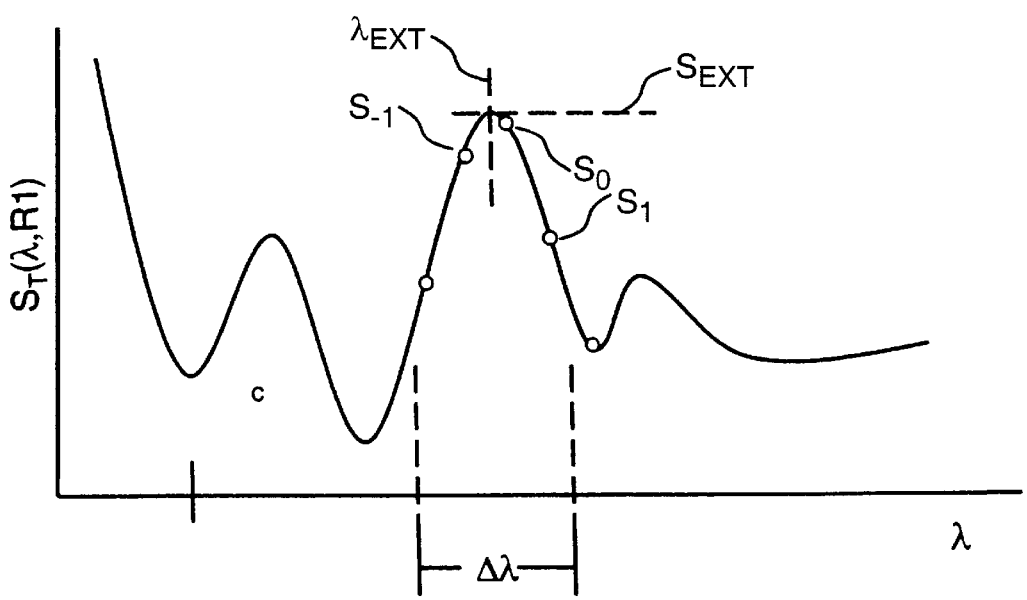
FIG._12A
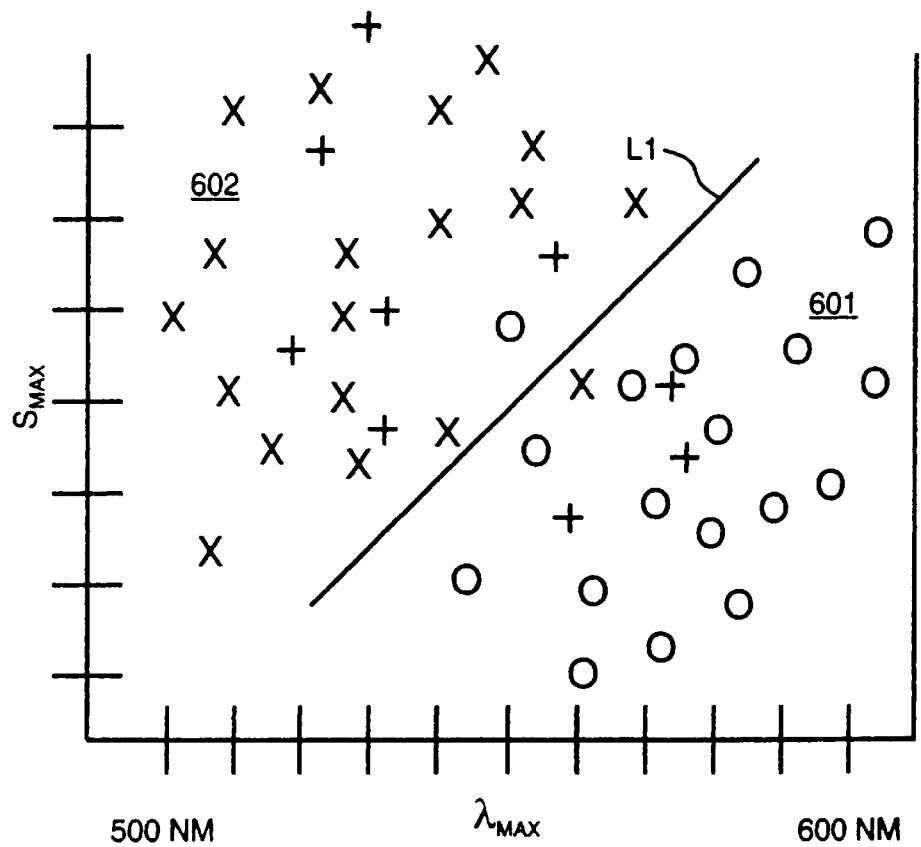
FIG._12B

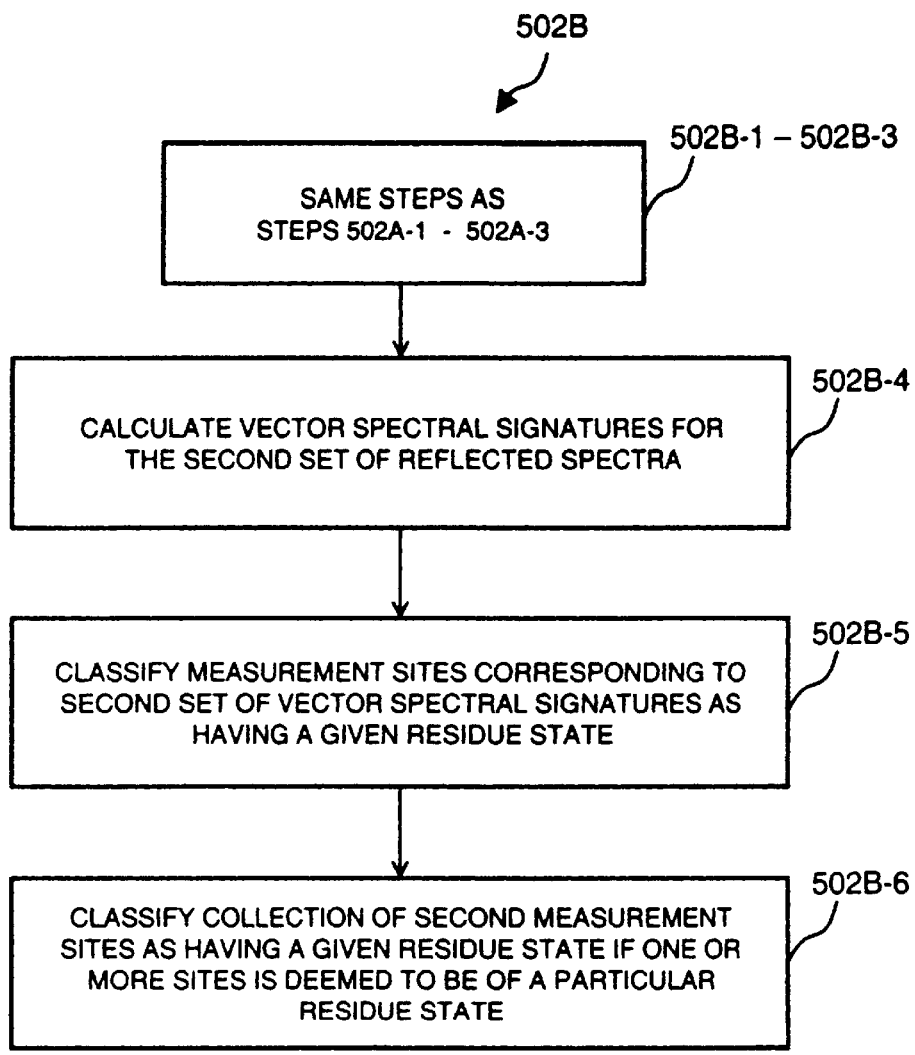
FIG._13
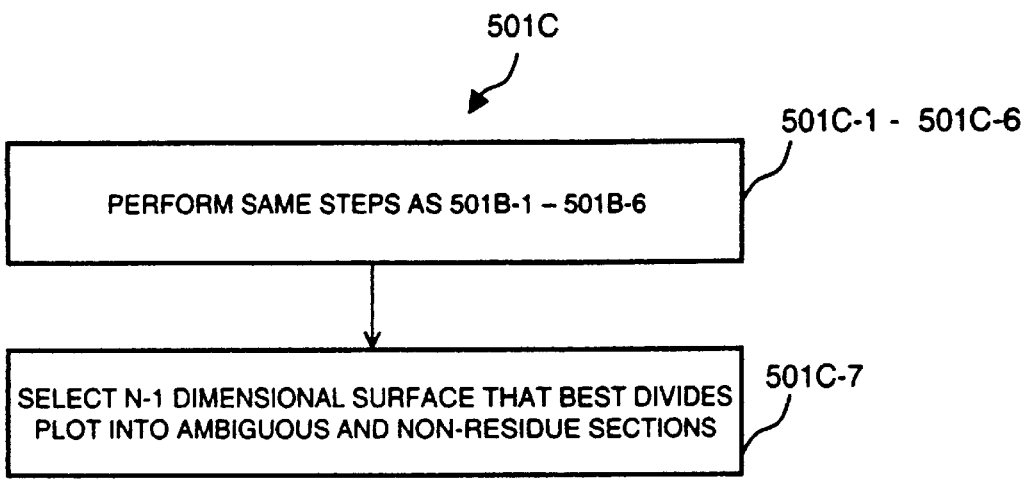
FIG._14

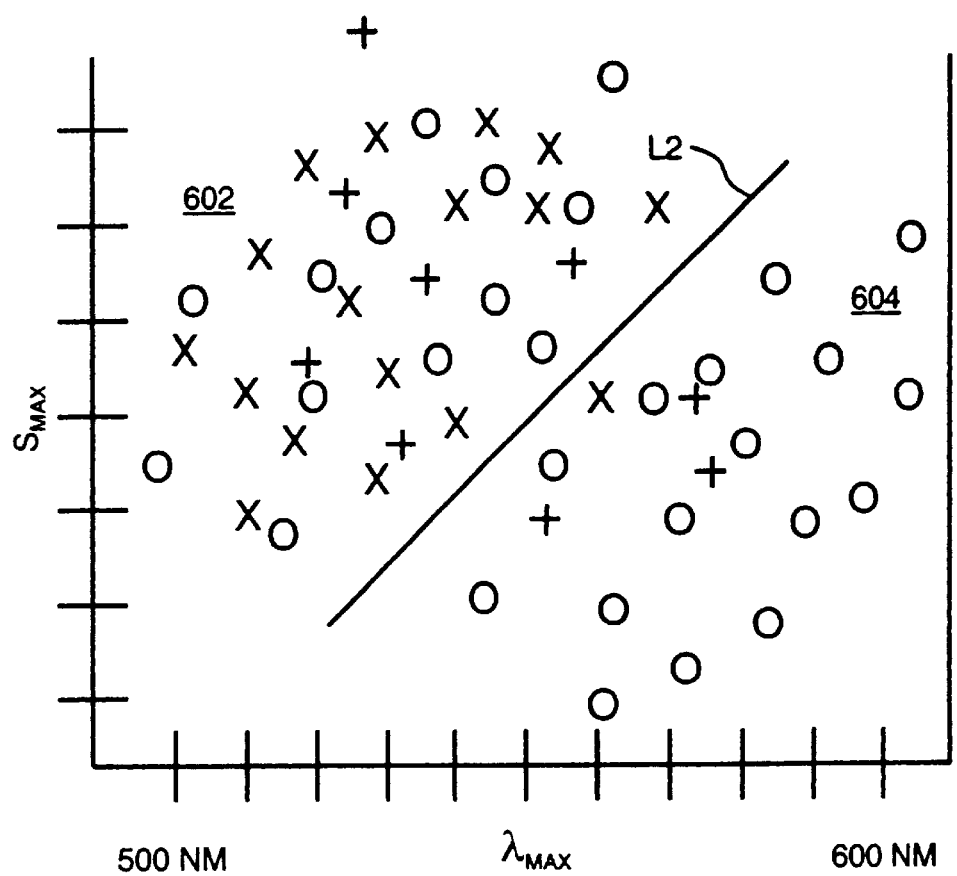
FIG._15
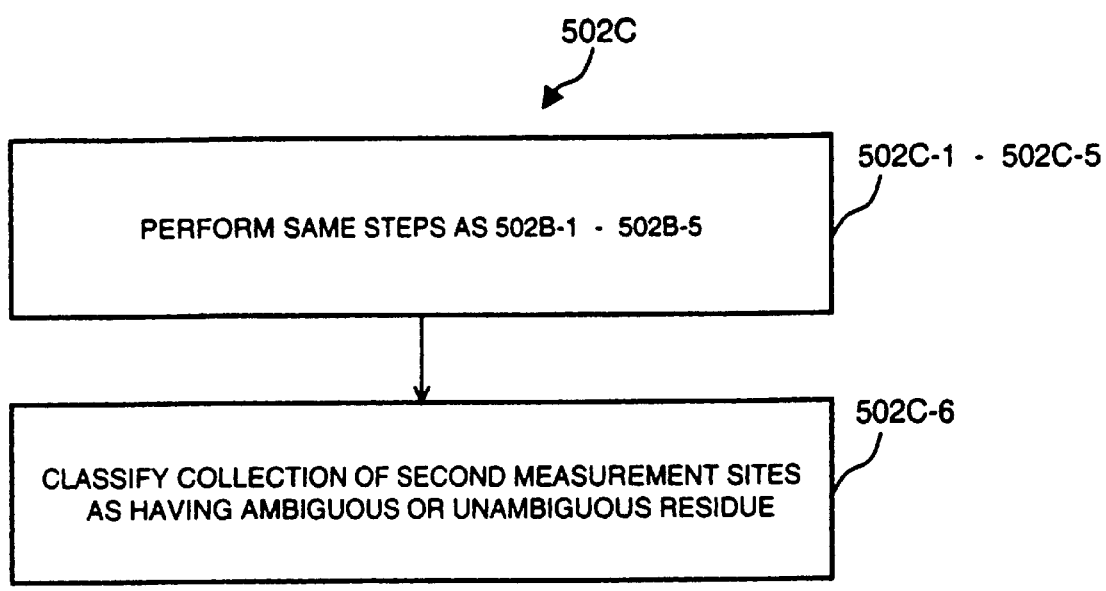
FIG._16A

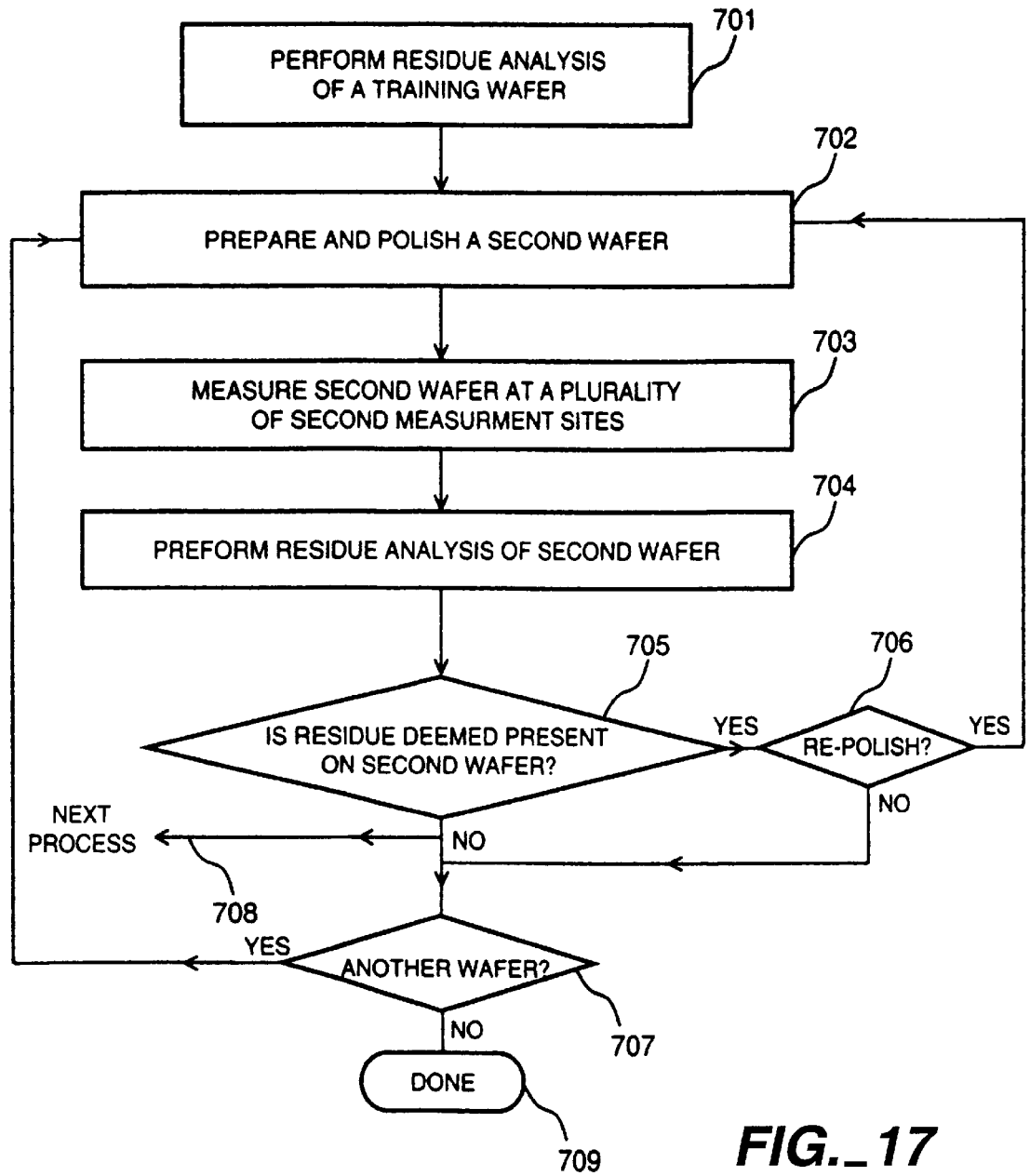

METHOD OF DETECTING RESIDUE ON A POLISHED WAFER

CROSS-REFERENCE TO RELATED APPLICATION

The application relates to and claims priority from U.S. provisional application Ser. No. 60/224,827, filed Aug. 11, 2000.

TECHNICAL FIELD

The present invention pertains to processing wafers, and in particular to detecting states on the wafers indicative of the quality of the processing.

BACKGROUND ART

Chemical-mechanical polishing (CMP) is a well-known process in the semiconductor industry used to remove and planarize layers of material deposited on a semiconductor device to achieve a planar topography on the surface of the semiconductor device. To remove and planarize the layers of the deposited material, including dielectric and metal materials, CMP typically involves wetting a pad with a chemical slurry containing abrasive components and mechanically polishing the front surface of the semiconductor device against the wetted pad to remove the layers of deposited materials on the front surface of the semiconductor device and planarize the surface.

FIG. 1 is a schematic view of a prior art CMP apparatus 10. In FIG. 1, CMP apparatus 10 includes a wafer carrier 11 for holding a semiconductor wafer 12 having a surface 12S to be polished. Wafer carrier 11 is mounted for continuous rotation about an axis A1 in a direction indicated by arrow 13 via a drive motor 14 operatively connected to the wafer carrier. Wafer carrier 11 is adapted so that a force indicated by arrow 15 is exerted on semiconductor wafer 12.

CMP apparatus 10 also includes a polishing platen 16 mounted for continuous rotation about an axis A2 in a direction indicated by arrow 17 by a drive motor 18 operatively connected to the polishing platen. A polishing pad 19, formed of a material such as blown polyurethane, is mounted to polishing platen 16. A polishing slurry containing an abrasive fluid, such as silica or alumina abrasive particles suspended in either a basic or an acidic solution, is dispensed onto polishing pad 19 through a conduit 20 arranged adjacent the polishing pad, from temperature controlled reservoir 21.

Wafer carrier 11 rotates in a direction indicated by arrow 13 about axis A1. Polishing platen 16 rotates in a direction indicated by arrow 17 about axis A2. The polishing slurry is dispensed onto polishing pad 19 through conduit 20, from temperature controlled reservoir 21 as the wafer carrier and polishing platen rotate about their respective axes. The force between the polishing platen and the wafer carrier and their relative rotation, in combination with the mechanical abrasion and chemical effects of the slurry, serve to polish wafer surface 12S.

FIG. 2 illustrates a semiconductor device prior to CMP. As shown, substrate 12 has a source region 112 and a drain region 114, and also includes lightly doped drains 116 and 118. Source and drain regions 112 and 114 are formed according to conventional processes, after formation of a gate oxide layer 122 and gate 124. Following formation of gate 124, a first inter-level dielectric (ILD) layer 120 is deposited over gate 124. First ILD layer is 120 formed of silicon dioxide, but may be formed of other dielectric materials.

After formation of first ILD layer 120, the layer is etched to form an opening that is filled with tungsten to form a contact plug 126, which provides ohmic contact to source region 112. Although not shown in the plane of the cross-section of FIG. 2, a similar contact plug is formed for drain region 114.

Thereafter, a first metal layer 128 is deposited on first ILD layer 120. First metal layer 128 is formed of a metal, such as copper, aluminum, or tungsten. A second ILD layer 130, an etch stop layer(not shown), and a third ILD layer 134 are then consecutively formed on the first metal layer 128. Layer 130, the etch stop layer and layer 134 are formed, patterned and etched according to conventional techniques to form openings, particularly via holes 136a and trenches 138a, via holes 136a being contiguous with respective trenches 138a. That is, each via hole shares a common, upper boundary at the interface between the via hole and the trench, where the via opens into the trench. According to the structure shown, a dual-inlaid process is used to deposit a second metal layer 139 simultaneously within via holes 136a and trenches 138a to form vias 136 and interconnects 138 (i.e., lines). The third ILD layer 134 includes fine pitch dielectric portions 134a separating the interconnects 138 from each other. Second metal layer 139 may be copper, aluminum or tungsten. In each case, the metal is put down in layer form on the order of 3,000 to 11,000 angstroms in thickness.

Once the basic structure of FIG. 2 is in place, CMP is carried out using CMP apparatus 10 of FIG. 1 to remove that portion of metal layer 139 above trenches 138a such that the trenches 138a form separate interconnects 138, and the exposed surface of the semiconductor device is polished and planarized for subsequent deposition steps, such as higher-level metal interconnects. With reference now to FIG. 3A, it is preferred that metal layer 139 be removed by polishing such that dielectric portions 134a separate trenches 138, with upper surface 12S being planarized. With reference now to FIG. 3B, it often occurs that some of the metal layer 139 is not entirely removed, leaving a "residue" 150 of material (here, a portion of metal layer 139). Generally, residue is any material that is supposed to have been removed from the surface of the wafer during processing.

The presence of residue 150 is problematic because it is not part of the planned semiconductor structure and thus will, in all likelihood, interfere with the performance of the resulting device. For example, in FIG. 3B, residue 150 short-circuits interconnects 138. Thus, the wafer shown in FIG. 3B would need to be re-polished, re-processed, or scrapped, unless the amount of residue was deemed minimal enough to allow the wafer to continue on to the next process.

Unfortunately, the most effective method presently available for determining if residue is present on a wafer appears to be visual inspection of the wafer surface after it has been polished. This is a time-consuming and labor-intensive process. Accordingly, it would be preferred to have an automated, time-saving way to assess the presence or absence of residue.

One approach to measuring residue is to treat the thin layer of typically metallic residue as a transparent film, and to measure its thickness as part of an homogenous film stack with an instrument like the KLA/Tencor UV1050. This method has several general requirements that constrain its utility. The underlying transparent stack must be known and information pertaining to the stack entered into the thin film instrument's recipe. The required information is at least nominal values for the thicknesses and optical properties of the stack. Acquiring this information and entering it into the instrument tends to be time consuming, and difficulties often arise with respect to gaining access to the relevant data. Also, the region where the residue measurement is made must be laterally homogeneous, i.e., the stack must include only flat layers that are substantially uniform over the dimensions of the spot size of the instrument. This is a serious limitation since the process in question may not leave residue over such homogeneous stacks, while leaving residue in other areas having heterogeneous structures with fine lateral dimensions. For example, residue 150 in FIG. 3B is in the vicinity of interconnects 138 which, in a modern integrated circuit, can have dimensions of 250 nm or less. Since these features are smaller than the wavelength of light, it is not possible to focus between the features, making this method unsuitable for measuring such residue.

DISCLOSURE OF THE INVENTION

The present invention pertains to processing wafers, and in particular to detecting states on the wafers indicative of the quality of the processing.

A first aspect of the invention is a method of determining the "state" of wafer. This could include, for example, first and second states corresponding to the presence and absence of residue, perhaps in the form of metal left on the surface of a wafer after chemical-mechanical polishing. The method comprises the steps of calculating first spectral signatures from a first set of measurement sites on one or more training wafers. The spectral signatures may be scalars or vectors. The measurement sites are each known to be of a particular state of two or more possible states. The two or more states may be residue states, i.e., states representing different amounts of residue on the wafer (including no residue). The next step involves correlating the first spectral signatures to the states, e.g., the presence or absence of residue on the training wafer(s). The next step then involves calculating second spectral signatures from a second set of measurement sites on a wafer where the states are unknown. The next step is to determine the states on the wafer based on the second spectral signatures. The determination of the states (e.g., presence or absence of residue) can also be done on an "ambiguous" and "non-ambiguous" basis. The next, optional step decides whether a wafer has residue based on the determinations at individual sites on the wafer. The final step controls the processing of this or subsequent wafers to minimize the occurrence or expense of an undesired state.

A second aspect of the invention is an apparatus for detecting states on a wafer having an upper surface. The apparatus comprises a stage for supporting the wafer, and a measurement unit for measuring reflected spectra from the wafer arranged adjacent the wafer upper surface. Further included is a control system electrically connected to the stage and the measurement unit. The control system is programmed to perform the steps of: first, calculating first spectral signatures from a first set of measurement sites on one or more training wafers, wherein the measurement sites are each known to be of a particular state of two or more states; then correlating the spectral signatures to the states; then calculating second spectral signatures from a second set of measurement sites on a wafer where the states are unknown; and then determining the states on the (unknown) wafer based on the second spectral signatures.

BRIEF DESCRIPTION OF THE DRAWINGS

FIG. 1 is a cross-sectional schematic diagram of a prior art CMP apparatus.

FIG. 2 is a prior art schematic cross-sectional diagram of a section of semiconductor structure in a wafer, illustrating the fabrication by CMP of tungsten contact studs embedded in silicon dioxide, with an upper layer of tungsten present prior to CMP polish.

FIG. 3A is the semiconductor structure of FIG. 2 after CMP polish is performed to achieve the desired planarization with the complete removal of the excess tungsten.

FIG. 3B is the semiconductor structure of FIG. 2 after CMP polish is performed, but with achieving the undesired result of having a portion of the tungsten metal layer remaining as "residue" atop the semiconductor structure.

FIG. 4 is a schematic diagram of a wafer polishing and measurement system of the present invention, which includes the CMP apparatus of FIG. 1 and an measurement unit for measuring the wafers after polishing.

FIG. 5 is a flow diagram of the two main steps involved in carrying out the methods of the present invention.

FIG. 6 is a flow diagram of the steps associated with a first embodiment of the first main step of FIG. 5.

FIG. 7 is an example plot of the reflected spectra for a location on training wafer having residue (dashed line) and a location on the training wafer having no residue (solid line).

FIG. 8 is a flow diagram of the steps associated with Step 501A-5 of the flow diagram of FIG. 6, for calculating a scalar spectral signature threshold value.

FIG. 9 is an example plot of a reflected spectrum from a training wafer from a particular measurement site R1, showing the maximum, the minimum, and the average over a selected wavelength range $\Delta\lambda$.

FIG. 10 is a flow diagram of the steps associated with a first embodiment of the second main step of FIG. 5.

FIG. 11 is a flow diagram of the steps associated with a second embodiment of the first main step of FIG. 5.

FIG. 12A is an example plot of $S_T(\lambda, R1)$ vs. $\lambda$ showing the estimate of an extremum $S_{EXT}$ within the chosen spectral range $\Delta\lambda$ by curve-fitting points in the vicinity of the extremum.

FIG. 12B is an example two-dimensional scatter plot of vector spectral signatures, showing the line separating the regions associated with residue being present and residue being absent.

FIG. 13 is a flow diagram of the steps associated with a second embodiment of the second main step of FIG. 5.

FIG. 14 is a flow diagram of the steps associated with a third embodiment of the first main step of FIG. 11.

FIG. 15 is an example two-dimensional scatter plot of vector spectral signatures, showing the line separating the regions associated with residue being present and residue being ambiguous.

FIG. 16A is a flow diagram of the steps associated with a third embodiment of the second main step of FIG. 11.

FIG. 16B is a flow diagram of the step associated with a third embodiment of the third main step of FIG. 11.

FIG. 17 is a flow diagram of the method of processing a wafer utilizing the residue detection methods of the present invention.

BEST MODE OF CARRYING OUT THE INVENTION

The present invention pertains to processing wafers, and in particular to detecting states on the wafers indicative of the quality of the processing.

Residue Detection Apparatus

With reference now to FIG. 4, there is shown a wafer polishing and measurement system 200 comprising a measurement unit 210 arranged adjacent a wafer stage 220 having an upper surface 224 capable of supporting a wafer W having an upper surface 230. Measurement unit 210 is fixed to a stage 232 capable moving in the X-Y plane in response to an electronic signal. Wafer stage 220 is preferably in operable communication with a drive motor 234 capable of causing rotation of the wafer stage in the X-Y plane about an axis A3 as indicated by arrow 235. Stage 232 is capable of moving wafer W with respect to measurement unit 210 in two dimensions, or alternatively, of moving the wafer in one dimension and measurement unit 232 in another. The dimensions of motion could be Cartesian (X and Y) or cylindrical R and Θ). In a preferred embodiment, stage 232 as shown in FIG. 4 provides primary motion in a radial direction R parallel to the X direction, and drive motor 234 provides rotary motion measured by angle Θ. Stage 232 also provides auxiliary motion in the Y direction to calibrate the motions. The primary calibration requirement is that the measurement spot of measurement unit 210 on the wafer passes through axis of rotation A3. The orientation of the measurement system with respect to system 200 and to world coordinates (e.g., "up" and "down"), as used above and in the following description, are for illustrative clarity only. For example, system 200 could be inverted or rotated by 90 degrees.

Wafer W is preferably a silicon wafer commonly used in the semiconductor industry for fabricating semiconductor devices. However, though the term "wafer" is used herein for ease of discussion, the method will be understood to apply generally to other types of substrates besides wafers, such as those used for storage-device heads, whereby residue needs to be detected after processing.

Measurement unit 210 may be a reflectometer assembly for measuring reflectivity (or a related property) of wafer upper surface 230. An exemplary reflectometer assembly is described in U.S. patent application Se. No. 09/533,613, filed Mar. 22, 2000, which is incorporated by reference herein. Measurement unit 210 may also be an ellipsometer capable of determining the phase difference Δbetween the parallel ($R_p$) and perpendicular ($R_s$) components of a light beam that has been elliptically polarized by reflection from wafer upper surface 230, while at the same time uniquely determining the ellipsometric parameter ψ of the elliptically polarized beam. Such ellipsometers are described in U.S. Pat. Nos. 4,053,232 and 5,166,752, which patents are incorporated by reference herein. Other suitable measurement units include a polarized reflectometer, such as described in the article by M. E. Lee, C. Galarza, W. Kong, W. Sun, and F. L. Terry, Jr., "Analysis of Reflectometry and Ellipsometry Data from Patterned Structures," International Conference on Characterization and Metrology for ULSI Technology, Gaithersburg, Md., Mar. 23–27, 1998, AIP Conference Proceedings 449, pp. 331–5 (1998), or a beam-profile reflectometer, such as described in U.S. Pat. No. 4,999,014, or any other reflectometer that measures the reflected intensity as a function of angles of incidence and reflection. Furthermore, combinations of such instruments would be suitable measurement units. In the latter case, the spectra described below would be combinations of data acquired by the component measurement systems.

Measurement unit 210 is thus described herein as being capable of measuring "reflected spectra" from upper surface 230 of wafer W. The term "reflected spectra" is used broadly and is meant to include any measurement made on the sample, such as detection of a signal as a function of wavelength that contains ellipsometric information, reflectivity information, or other such information obtainable by sensing reflected light from wafer W. More specific examples are profiles as a function of position, optical spectra as a function of wavelength, optical spectra as a function of angle, optical scattering as a function of angle, X-ray scattering, fluorescent spectra as a function of wavelength, etc. Also, any transform of such spectra is also considered as spectra in the present invention. This will particularly be the case when these spectra are transformed, possibly with other measured or known information, to calibrate the instrument or to increase the sensitivity of the raw measurements to the disposition of interest, e.g., the disposition of residue.

With continuing reference to FIG. 4, system 200 further includes a CMP apparatus 240, such as apparatus 10 of FIG. 1, and a wafer handling system 250 in operative communication with the CMP apparatus and wafer stage 220 (as indicated by the dashed arrows 244 and 246) for transferring wafers W between the CMP apparatus and the wafer stage (as indicated by the double arrow 248).

Apparatus 10 also preferably includes a control system 260 electrically connected to wafer handling system 250, CMP apparatus 240, wafer stage 220 and measurement unit 210. In a preferred embodiment, control system 260 is a computer having a memory unit MU with both random-access memory (RAM) and read-only memory (ROM), a central processing unit CPU (e.g., a PENTIUM™ processor from Intel Corporation), and a hard disk HD, all electronically connected. Hard disk HD serves as a secondary computer-readable storage medium, and may be, for example, a hard disk drive for storing information corresponding to instructions for control system 260 to control the devices connected thereto. Control system 260 also preferably includes a disk drive DD, electronically connected to hard disk HD, memory unit MU and central processing unit CPU, wherein the disk drive is capable of accepting and reading (and even writing to) a computer-readable medium CRM, such as a floppy disk or compact disk (CD), on which is stored information corresponding to instructions for control system 260 to carry out the method steps of the present invention. Control system 260 also preferably includes an input device ID for inputting information into the control system. An exemplary control system 260 is a computer, such as a DELL PRECISION WORKSTATION 610™, available from Dell Corporation, Dallas, Tex. Control system 260 is programmed to control the operation of the above-described elements making up system 200 to carry out the methods of the present invention, as described below.

Control system 260, CMP apparatus 240, wafer stage 220 and measurement unit 210 may be operated as an integrated system or in a stand-alone geometry with operable communication therebetween. Control system 260 can be a distributed control system comprised of separate but interconnected computers, e.g., one for the CMP apparatus, one for the measurement unit, etc. Control system 260, wafer stage 220 and measurement unit 210 constitute a residue detection apparatus according to the present invention.

Residue Detection Methods

The present invention comprises methods for detecting the "state" of residue of a wafer, as described below with reference to the flow diagrams of FIGS. 5, 6, 8, 10, 11, 14, 16A, 16B and 17. In the simplest case, which is described in detail, there are two (i.e., first and second) residue states: the presence and absence of residue on a polished wafer.

However, it will be understood that the description below applies generally to "n" residue states, where n is two or greater.

An overview of the method of the present invention is first presented, followed by increasing amounts of detail for each of the steps of the method. Three main method embodiments are presented, whose main difference involves the manner in which a spectral signature is determined, as described below.

Main Method Steps

With reference now to FIG. 5 and flow diagram 500, there is shown the two main steps of the method of the present invention for determining the presence or absence of residue on a wafer and processing subsequent wafers. Step 501 involves performing an empirical analysis of a first "training set" of measurement sites R1 (see FIG. 4) on one or more CMP polished "known" training wafer $W_T$, where, on some of the sites R1, residue is known to be present, while on others it is known to be absent. The analysis can be performed, for example, on first and second training wafers, where the first training wafer is known to have residue on its sites R1$a$ and the second training wafer is known not to have residue on its sites R1$b$. Alternatively, a whole cassette of wafers could be used to obtain training data. Also, an historical database based on periodic examination of wafers coming off a line could be built. The requirement is simply that there are measurements of spectral signatures at sites known to have residue or be clear. Similarly, for measurement Step 502 as discussed below, the set of measured sites might come from a cassette of wafers. The key is to have a set of sites with and without residue, i.e., with all the residue states of interest.

Step 501 includes obtaining spectral signatures and ranges for the sites R1 and correlating the spectral signatures to the presence or absence of residue. A "spectral signature," as the term is used herein, is any reduction of the spectra that serves to separate measurement sites according to their disposition as having residue or not having residue. "Clear" is used herein to describe a measurement site which does not have residue. Also used herein are the terms "ambiguous" and "unambiguous" in connection with the presence or absence of residue. These terms are meant to signify that the measurement indicating the presence or absence of residue has a low degree or high degree of uncertainty, respectively. Unqualified measurements are understood to be substantially unambiguous.

The second main step, Step 502, involves applying the results of the analysis of Step 501 from the training wafer(s) to a second set of measurement sites R2 on a second "unknown" wafer $W_U$, on which the residue state is unknown.

The third main step, Step 503, involves classifying the collection of sites R2 as being of a given residue state based on the individual classification in Step 502. In the simplest case, if one or more of sites R2 is deemed to have residue present, then the collection of sites is deemed to have residue present. In more complex situations, a probabilistic determination may be made, based on the probability of false determination of individual sites. This step is optional.

The fourth main step, Step 504, involves controlling the process based on the above mentioned determinations of state is the final step in the process. Several actions may be taken if the undesirable state, e.g., residue, is found. For example, the wafer may be reprocessed. The parameters of the process that produced the wafer may be adjusted to prevent future occurrences (on other wafers) of the undesirable state. The parameters of subsequent processes may be adjusted to compensate for the undesirable state on this wafer. The parameters of previous processes may be adjusted to prevent future occurrences (on other wafers) of the undesirable state. An example would be to reduce the deposition thickness of metal before the polishing step where residue is found. The wafer may be reexamined by a more dependable, but possible more expensive method.

First Main Method Step, First Embodiment

With reference now to FIG. 6 and flow diagram 501A, the details of a first embodiment for carrying out step 501 are set forth. Step 501A-1 involves preparing one or more training wafers $W_T$ by using a semiconductor process such as that described above in the "Background Art" section. Next, Step 501A-2 involves polishing the training wafer(s) $W_T$ such as in the manner as described above in the "Background Art" section using CMP apparatus 240.

Next, Step 501A-3 involves inspecting training wafer(s) $W_T$ at the first set of measurement sites R1 to obtain data identifying the residue states (e.g., the presence or absence of residue) at the sites. Measurement sites R1 can be predetermined based on the particular semiconductor device process used to prepare training wafer $W_T$ in step 501A-1, or can be chosen afterward. Typically, measurement sites R1 will cover the inner and outer portions of training wafer $W_T$ to ensure that an adequate sampling of the wafer is obtained. The inspection of the measurement sites R1 is preferably conducted visually using one of a number of microscopes employed in semiconductor manufacturing to inspect wafers, such as an Olympus microscope, model BH3-MJL, available from the Olympus Corporation. The microscope should have resolution adequate to clearly discern the presence or absence of residue. Alternatively, the inspection of training wafer $W_T$ is conducted using electrical measurements. This inspection step can be performed after some of the following steps. Also, step 501A-3 can be destructive. For example, destructive inspection in step 501A-3 may comprise the steps of sectioning the wafer, imaging the cross section, and inspecting the image. Other inspection methods are possible, such as other types of spectroscopy that can differentiate trace amounts of elements or materials (e.g., metal, oxide, etc.) constituting residue.

Next, Step 501A-4 involves measuring a first training set of reflected spectra at the first set of training sites R1. This is accomplished by control system 260 sending an electronic signal to wafer stage 220 directing the stage to move in the x-y plane to each of the measurement sites. Control system 260 activates measurement unit 210 at each of the measurement sites R1 to obtain reflected spectra at each site as a function of wavelength, thereby forming a training set of reflected spectra $S_T(\lambda, R1)$ that is a function of wavelength $\lambda$ and measurement site R1. The reflected spectra are recorded as discrete points and stored in memory unit MU in control system 260.

With reference now also to FIG. 7, two reflected spectra are shown plotted as curves C1 and C2, with curve C1 taken from a measurement site where residue is absent (solid line), while curve C2 is taken from a measurement site where residue is present (dashed line). The two spectra $S_T((\lambda, R1)$, represented by curves C1 and C2, differ significantly from each other, providing a way of determining whether residue is present or absent.

Next, step 501A-5 involves calculating a scalar spectral signature value D for some or all of the first set of training sites R1. A preferred method of calculating spectral signature values D from the first set of training reflected spectra $S_T(\lambda, R1)$ obtained in step 501A-4 is described now with reference to FIG. 8 and flow diagram therein. Steps 501A-5A through 501A-5D involve performing the following calculation for each reflected spectrum $S_T(\lambda, R1)$:

$$a(R1) = \text{MAX}_{\Delta\lambda}(S_T(\lambda, R_1)) \quad [\text{EQ. 1}]$$

$$b(R1) = \text{MEAN}_{\Delta\lambda}(S_T(\lambda, R1)) \quad [\text{EQ. 2}]$$

$$c(R1) = \text{MIN}_{\Delta\lambda}(S_T(\lambda, R1)) \quad [\text{EQ. 3}]$$

$$D(R1) = [(a-b)/(b-c)] - 1 \quad [\text{EQ. 4}]$$

With reference to FIG. 9, in the above equations, a (R1) represents a local maximum value of $S_T(\lambda, R1)$ as a function of $\lambda$, b(R1) represents the mean value of $S_T(\lambda, R1)$ as a function of $\lambda$, and c (R1) represents a local minimum of $S_T(\lambda, R1)$ as a function $\lambda$, over a pre-selected wavelength range $\Delta\lambda$.

With reference again to FIG. 6, once the spectral signature values D are calculated, then Step 501A-6 involves correlating the data obtained in Step 501A-3 to the calculated spectral signature values D obtained in Step 501A-5. The goal is to identify a spectral signature threshold value $D_{TH}$ delineating the residue states (e.g., the presence or absence of residue). Thus, spectral signature values $D > D_{TH}$ correspond to residue being present for the case considered here and spectral signature values $D > D_{TH}$ correspond to residue being absent. Spectral signature threshold value $D_{TH}$ will typically not be an absolute threshold, i.e., not all values on either side of $D_{TH}$ will absolutely satisfy the above conditions for residue being present or absent. Rather, $D_{TH}$ is chosen as a "best choice" value such that the spectral signatures falling on either side of $D_{TH}$ best represent the true condition of residue being present or absent as determined in Step 501A-3. Thus, $D_{TH}$ is chosen so that the number of spectral signatures D falling on the correct sides of $D_{TH}$ is maximized, or optimized by some other criterion.

Threshold $D_{TH}$ may be selected such that it gives preference to the false determination of one state over another. There is generally a tradeoff, in that moving the threshold toward the mass of residues will result in more false clears and fewer false residues, and vice versa. One could opt for equal probability of each type of false indication, or allow for some preference. For example, a "no false clears" strategy may be a desirable for process control because it will not let "bad" (i.e., residue-present) wafers through. This strategy will generate more false residues. From the point of process control, this may be acceptable because the false determination of residue can be corrected by re-inspecting the wafer or taking remedial action (e.g. re-polishing). Remedial action is appropriate when the remedial activity is not excessively costly in terms of process time or device performance. Device performance is an issue because the remedial activity could be excessive activity, i.e., based on a false determination of residue. If remedial action is too costly, reinspection is an appropriate option: all wafers that are determined to have the undesirable state (i.e., residue) can be visually inspected before remedial action is taken, or before they are scrapped. Even though visual inspection is costly, and the method described here uses it, the method substantially reduces the number of wafers that need to be visually inspected.

Second Main Method Step, First Embodiment

With reference now to FIG. 10 and flow diagram 502A, the steps involved in carrying out Step 502A according to a first embodiment of the present invention are now discussed in greater detail. Step 502A-1 involves preparing a second wafer to be measured $W_M$, using the same or similar semiconductor process as the first semiconductor process used for training wafer $W_T$ in Step 501A-1. Next step 502A-2 involves polishing the wafer using CMP apparatus 240 in the same or similar manner as training wafer $W_T$ is polished according to Step 501A-2.

Wafer $W_M$ is then transferred from CMP apparatus 240 to wafer stage 220 via wafer handling system 250 under the operation of control system 260. Then, next step 502A-3 involves measuring a second set of reflected spectra $S_M(\lambda, R2)$ at a second set of measurement sites R2. 'Wafer' is construed to be any sample which encompasses the second set of measurement sites R2, i.e., it may actually be a cassette of wafers or the substrate for thin-film heads used in magnetic recording. Measurement sites R2 may be the same as measurement sites R1, have some sites in common with measurement sites R1, or be completely different from measurement sites R1. Typically, all sites R1 and R2 will be similar in the sense that they are designed to be the same, even though they may differ substantially due to process variations. Wafers are typically divided into dies that will become individual devices. Typically, these dies are all designed to be the same, especially in the device or active region of the dies. Thus, corresponding points in dies will be similar, as defined above. Also, there can be similar points within a single die, i.e., two capacitors that have the same design will yield similar measurement locations. Wafers are typically patterned on a lithographic stepper, which exposes one stepper field at a time. Each stepper field is thus intended to be identical, so that corresponding points within stepper fields are similar. Frequently, test structures are placed in the scribe lines between dies. These may or may not repeat for every die, but do repeat for every stepper field, and thus would be similar points for stepper fields but not for dies.

Measurement of the second set of reflected spectra is accomplished by control system 260 sending an electronic signal to stage 232 directing measurement unit to move to each of the measurement sites R2 in the second set of measurement sites, and then activating measurement unit 210 to obtain reflected spectra $S_M(\Delta, R2)$ at each site as a function of wavelength. This results in a second set of reflected spectra $S_M(\lambda, R2)$ that is a function of wavelength $\lambda$ and measurement sites R2.

Next Step 502A-4 involves calculating scalar spectral signatures D' for the second set of reflected spectra $S_M(\lambda, R2)$ using the same steps as described in Step 501A-5 (see FIG. 8). Then, in Step 502A-5, the calculated spectral signatures D' for the second set of reflected spectra $S_M(\lambda, R2)$ are compared to the spectral signature threshold value $D_{TH}$ as deduced in Step 501A-6. Based on this comparison, the corresponding measurement site R2 is classified into different residue states, i.e., as either having residue present ($D' > D_{TH}$) or residue absent ($D' < D_{TH}$).

Third Main Method Step, First Embodiment

The first embodiment of the third main step is to assign a state of residue to the wafer if one or more of the measurement sites on the wafer are deemed to have residue.

Fourth Main Method Step, First Embodiment

With reference now to FIG. 17 and also to system 200 of FIG. 1, exemplary steps for processing wafers according to Step 504 in FIG. 5, using the methods as described above and wafer polishing and measurement system 200 of FIG. 4 are now described with reference to flow diagram 700.

Step 701 involves performing a residue analysis of a training wafer $W_T$, as described above in connection with the first and second embodiment of performing Step 501 of flow diagram 500 of FIG. 5. Then, next Step 702 involves preparing and polishing a second wafer to be processed, along the lines described in connection with Steps 502A-1 and 502A-2 of flow chart 502A of FIG. 10.

The next Step 703 involves measuring the second wafer (e.g., wafer $W_M$, discussed above) at a plurality of second measurement sites, as described above in connection with Steps 502A-3 through 502A-5 of FIG. 10. The next Step 704 performs a residue analysis of the second wafer, as described in connection with Step 503 of FIG. 5. This may involve a "scalar" analysis, as described in connection with the first embodiments of main Steps 501 and 502, or a "vector" analysis, as described below in connection with the second embodiments of main steps 501 and 502. Based on the outcome of the analysis of Step 704, a decision is made in query Step 705 as to whether residue is deemed present or absent from the wafer. If residue is deemed present, then the method proceeds to Step 706, which is a query step asking whether the wafer should be re-polished. If the answer to Step 706, is "yes", then the wafer returns to Step 702 and is re-polished. If the answer to Step 706 is "no", then the process terminates for that wafer, and the method proceeds to Step 707, which asks if another wafer is to be processed.

On the other hand, if the residue is deemed absent from the wafer, then the wafer is sent on to the next step in the semiconductor process, as indicated by arrow 708. The next Step is then the aforementioned query Step 707, inquiring whether another wafer is to be prepared and processed. If the answer is "yes", then the method returns to Step 702 where the next wafer is prepared and polished, and the Steps of flow diagram 700 are repeated. If no other wafers are to be processed, then the method proceeds to Step 709, and is "done".

In addition to, or alternatively to, the process described above for re-polishing a wafer, the determination of residue present on a wafer can be used to control the process for subsequent wafers. If there is residue present on wafer N, then the polishing time for wafer N+M should be increased by some amount. This control algorithm could additionally use other information recorded from the process tool or wafer, e.g., the level of erosion present on the wafer, or the current polishing force in use.

First Main Method Step, Second Embodiment

The present invention includes a second embodiment for the first main method step (Step 501) similar to the first embodiment for this step as described above. Thus, only the differences in the second method embodiment from the first method embodiment are described.

With reference now to FIG. 11A and flow diagram 501B, Steps 501B-1 through 501B-4 are the same as Steps 501A-1 through 501A-4. However, rather than calculating scalar spectral signatures as a scalar quantity in Step 501A-5 using Equations 1 through 4 (see FIG. 8), in Step 501B-5 the spectral signature takes the form of a vector quantity that is calculated from the reflected spectra $S_T(\lambda, R1)$. This is done, for example, by first choosing a spectral range $\Delta\lambda$ (i.e., a range of wavelengths $\lambda$) for a given reflected spectrum $S_T(\lambda, R1)$. The spectral range $\Delta\lambda$ is chosen by observing spectra features (e.g., maxima, minima and inflection points) and selecting a range that captures at least one such feature. The process, as described below, is then carried out with the selected wavelength range and tested for false results (e.g., a finding of residue present, when in fact none is present). This process may be repeated with alternative definitions of the vector spectral signature to attempt to minimize the number or probability of false results. For example, a different extremum in a different spectral range $\Delta\lambda$ could be tested to see if it yields fewer or no false results. Other very different spectral signatures, as described below, can also be tested and compared.

Next, Step 501B-5 for this example further includes estimating an actual extremum $S_{EXT}$ within the chosen spectral range $\Delta\lambda$ by curve-fitting the points in the vicinity of the extremum as shown in FIG. 12A. The maximum sample in the range $\Delta\lambda$ is $s_0$. Its neighboring samples are $s_{-1}$ and $s_1$. Then, the actual value of the extremum $S_{EXT}$, and the wavelength associated with the extremum $\lambda_{EXT}$ are estimated from fitting a parabola to the three samples identified above and constitute the spectral signature, as a coordinate pair or vector $D=(S_{EXT}, \lambda_{EXT})$, for a given measurement site R1.

Other like coordinates could be included so that the spectral signature D is not just a two-dimensional vector, but is N-dimensional. Several examples are given below:

$D=(S_{EXT1}, S_{EXT2})$
$D=(S_{EXT1}, S_{EXT2}, S_{EXT3})$
$D=(S_{EXT1}, S_{EXT2}, \lambda_{EXT1})$
$D=(S_{EXT1}, \lambda_{EXT1}, C_{EXT1})$, where C denotes the curvature of the spectrum in the vicinity of the extremum.

Other possible dimensions include: mean, median, quartiles or other percentile values, as well as spectral moments. Transforms of the spectra yield another class of dimensions. Examples of the latter include the peak value or peak location of a Fourier spectrum of the measured spectrum after it has been preprocessed to minimize 'end effects', as is known in the art. The book *The Fourier Transform and Its Applications* by Bracewell provides other examples of useful transforms of this type, and the book *Image Analysis and Mathematical Morphology* by J. Serra provides examples of so-called morphological transforms applicable to the present invention. Such transforms would include transforms intended to reduce spectral noise by smoothing the spectrum. Yet another class of dimensions are the parameter of functions fitted to the spectrum. Examples of such functions would be polynomials, rational functions, trigonometric functions and combinations of such. Thus, the method encompasses the standard methods of measuring film thicknesses from optical spectra, which is well known in the art.

Next, with reference also to FIG. 12B, Step 501B-6 involves considering each spectral signature vector D in the appropriately N-dimension space. FIG. 12B shows a plane for a two-dimensional spectral signature vector D. The plot of FIG. 12B is a type of scatter plot. The "x's" in the plot indicate a spectral signature vector D known to represent a measurement site R1 where residue is present, and the "o's" in the plot indicate a spectral signature vector D known to represent a measurement site R1 where residue is absent. Then, Step 501B-7 involves selecting a curve in the case of two-dimensions (or more generally, an N−1 dimensional surface), indicated in FIG. 12B by the curve L1. Curve L1 is the curve that best divides the plot in FIG. 12B into a first section 601 containing mostly or exclusively points representing "no residue" at certain sites R1 and a second section 602 containing mostly or exclusively points representing "residue" at certain sites R1. The selection of curve L1 can be done by "eye" or by computer program that chooses the best dividing surface ("curve") for the data. As mentioned above, the choice of curve L1 may be biased by process-control considerations.

Here, "curve" is used to signify some hyper-surface that separates two hyper-volumes in an N-dimensional space. The curve's overall shape can be constrained based on the nature of the data and the states that are to be separated. Typically, the curve will be smooth relative to the scale of the sampling of points in the hyper volume. The goal is that surface is constrained such that deviations from smoothness not pick out small clusters or single points whose known (residue) state may not be characteristic of the state of other points in the immediate vicinity, i.e., due to noise in the spectral data. Other examples of curves on a plane could be circles, parabolas, hyperbolas, ellipses, polygons, polynomials, spline curves, etc. (or sections thereof, when appropriate). A curve may be a collection of segments composed of the aforementioned curves. Generalizations of these to N dimensions, possibly combining several to describe different dimensions are understood to be in the class of acceptable surfaces, e.g., a sphere, a parabola rotated about an axis, or an ellipse extended along an axis perpendicular to the ellipse. Again, the N−1 dimensional curve can be composed of segments of simpler curves, e.g., in 3 dimensions, the curve could be composed of intersecting planes. The list of shapes above is not intended to comprise a complete set of the shapes suitable for this application, but rather to indicate the wide range of possibilities that suitable.

Second Main Method Step, Second Embodiment

With reference now to FIG. 13 and flow diagram 502B, once main Step 501 of FIG. 5 is complete, then the method proceeds to main step 502 of applying the results of the second embodiment of carrying out Step 501, as described immediately above, to a second unknown wafer to be measured (e.g., wafer $W_M$)

In flow diagram 502B of FIG. 13, Step 502B-1 through Step 502B-3 are the same as Steps 502A-1 through Steps 502A-3. Then, next Step 502B-4 involves calculating vector spectral signatures D' for the second set of reflected spectra $S_M(\lambda, R2)$, in the same manner as described above for the first (teaching) set of reflected spectra $S_T(\lambda, R1)$. Then, with reference again to FIG. 12, Step 502B-5 involves the same process of comparing (e.g., plotting) the vector spectral signatures D' (as indicated by "+'s" in FIG. 12) to the position of the N−1 dimensional surface (e.g. curve L1) and classifying the measurement sites R2 corresponding to the second set of vector spectral signatures D' as having a given residue state (e.g., residue present or absent).

Note that the second embodiment for the first and second main method steps is a generalization of the first embodiment. The second embodiment with N=1, and N−1=0 reduces to the first embodiment. In fact, the second embodiment is considered herein as a "vector" model and the first embodiment is considered as a "scalar" model. Thus, the spectral signature threshold quantity can be either a vector or a scalar.

First Main Method Step, Third Embodiment

The present invention includes a third embodiment for the first main method step (Step 501) similar to the first embodiments described above. Thus, only the differences in the third method embodiment from the first and second method embodiments are described.

With reference now to FIG. 14 and flow diagram 501C, Steps 501C-1 through 501C-6 are the same as Steps 501B-1 through 501B-6.

Next, with reference also to FIG. 15, Step 501C-6 involves considering each spectral signature vector D in the appropriately N-dimension space, where N is greater than zero. FIG. 15 shows a plane for an exemplary two-dimensional spectral signature vector D. The plot of FIG. 15 is a type of scatter plot. The "x's" in the plot indicate a spectral signature vector D known to represent a measurement site R1 where residue is absent, and the "o's" in the plot indicate a spectral signature vector D known to represent a measurement site R1 where residue is present.

In the previous (second) embodiment, it is possible to substantially separate the two residue states with a smooth curve. This clear delineation between states is the most desirable situation. However, in the present third embodiment involving the data represented in FIG. 15, clear delineation between residue states is not possible, as the spectral signatures from the two states are mixed up. This creates ambiguity with regard to the residue states. Nevertheless, it is possible to obtain useful information about the likelihood that the wafer is of a particular residue state, e.g., does or does not have residue.

Thus, in this third embodiment, Step 501C-7 involves selecting a curve in the case of two dimensions (or a point in the case of one dimension, or more generally, an N−1 dimensional surface), indicated in FIG. 15 by the curve L2. Curve L2 is the curve that best divides the plot in FIG. 12 into a first, ambiguous section 602 containing points representing "no residue" and "residue" at certain sites R1 and a second section 604 containing substantially all points representing "residue" at certain sites R1. The selection of curve L2 can be done by "eye" or by a computer program that chooses the best dividing surface for the data. The goal in choosing the delineating curve L2 is to claim as much space as possible for the unambiguous residue region 604 corresponding to a first residue state (e.g., residue present) while including substantially no training spectral signatures corresponding to sites of a second residue state (e.g., residue not present). Having an ambiguous region 602 is unavoidable given the disposition of the spectral signatures: points representing both residue states are interspersed and cannot readily (if at all) be separated by a smooth curve.

Second Main Method Step, Third Embodiment

With reference now to FIG. 16A and flow diagram 502C, once main Step 501C of FIG. 14 is complete, then the method proceeds to step 502C of applying the results of the third embodiment of carrying out Step 501C, as described immediately above, to a second unknown wafer.

In flow diagram 502C of FIG. 16A, Step 502C-1 through Step 502C-5 are the same as Steps 502B-1 through Steps 502B-5. Then, next Step 502C-6 involves the same process of comparing (e.g., plotting) the vector spectral signatures D' (as indicated by "+'s" in FIG. 15) in the N-dimensional space to the position of the N−1 dimensional surface (e.g. curve L2), and classifying the measurement sites R2 corresponding to the second set of spectral signatures D' as having ambiguous or unambiguous residue present.

Third Main Method Step, Third Embodiment

Once the measurement sites are classified as ambiguous or unambiguous, next Step 503C involves classifying the collection of sites R2 as having residue if one or more of sites R2 is deemed to have unambiguous residue present.

The utility of this method can be appreciated, and the choice of L2 made by considering the following analysis. For this example, it is assumed that the set of sites R2 are on a particular wafer and are intended to characterize the results of processing that wafer. For the set of sites R2 having known residue, a number $N_A$ of these sites fall in the ambiguous region 702, and a number $N_u$ of these sites fall in the unambiguous region 704. There is a probability p that any site on the wafer that actually has residue is ambiguous as far as the optical measurement is concerned. This probability can be approximated by $$p = N_A/(N_A + N_U).$$  [EQ. 5]

The probability that all $N_R$ sites with residue on a wafer will be ambiguous is $$P = p^{\{N_R\}}$$  [EQ. 6]

Thus, the probability that a wafer will be falsely identified as being "clear" i.e., residue-free, is the probability p that a site with residue is ambiguous raised to the power equaling the number of measured sites that actually have residue. The probability of a wafer being falsely identified as having residue is the probability that at least one of the sites identified as unambiguously having residue is, in fact, clear. Such a case is represented in FIG. 15 by the one "x" in region 704. Curve L2 is best chosen by simultaneously minimizing the probability that $N_R$ sites will appear ambiguous and the probability that at least one of the ambiguous sites is actually clear. Increasing the number of measurements on the wafer improves the ability to distinguish between cleared and uncleared wafers. Choosing the measurement sites where residue is deemed likely improves the ability to distinguish between cleared and uncleared wafers. Moving the curve L2 away from the mass of cleared points increases the probability of a false indication of a clear wafer. Moving the curve towards the mass of cleared points increases the probability of a false indication of a wafer with residue. Again, the choice of the curve delineating residue states may be biased by process-control considerations, as described above, but with the ambiguous state.

Computer Control of the Methods Through Software

The methods as described above can be implemented in apparatus 200 by programming control system 260 to carry out the steps associated with the methods. These steps may be in the form of software, i.e., instructions stored in computer readable medium CRM, which is loaded into disk drive DD of control system 260. The instructions can then be stored in memory unit MU, along with additional information needed to carry out the steps of the method. This additional information may be input into control system 260 via input device (e.g., keyboard) ID.

Process Applications with More Than Two Residue States

The present invention addresses the need to identify different residue states on a wafer using non-destructive inspection of the wafer consequent to one or more wafer processing steps. The embodiments above describe applications to chemical mechanical polishing of a metal layer where there are two residue states of interest: the presence or absence of residue. One such example involves chemical mechanical polishing of shallow trenches used for isolation of transistors in integrated circuits. One application for this process is to detect a residue of oxide on top a nitride area that protects the active regions of the device from the etching for the shallow trench.

However, as discussed above, identifying more than two residue states might be preferred for different wafer processing situations. For example, in the case where there is a thin layer of barrier material deposited before metal layer 139 in FIG. 3B, there could be as many as four residue states: a first state of no residue present, a second state where barrier residue is present, a third state where barrier residue plus metal residue is present, and fourth state where only metal residue is present. The latter state occurs where the CMP process has smeared metal from one location on the wafer to another.

Another wafer processing scenario amenable to identifying more than two residue states pertains to chemical mechanical polishing of metal and distinguishing residues having different thicknesses. This involves subdividing the "with residue" state into several states (e.g., sub-states) of lesser and greater thicknesses of residue. The advantage of this method over a film thickness measurement is that it requires purely empirical data more readily available in a manufacturing environment.

Thus, the above-described invention has been described generally for the case of two residue states for the sake of explanation, but will be understood to apply to cases where there are more than two residue states.

Further Applications

Two alternative processes that could benefit from the method of the present invention are etch and lithography processes. One application within etch would be comparable to that described above for chemical mechanical polishing to detect the presence or absence of material that should have been cleared by the etch processes. Another application within etch would be to detect whether trenches etched without a stop layer are the correct depth. Here, the set of states would be "depth" states, wherein the first state is "too shallow," the second state is "correct depth" and the third state is "too deep." The inspection of step 501A-3 in this case would be done destructively after the optical measurements of step 501A-4. An application for lithography of this invention would be to detect incomplete development of photoresist resist on the wafer. The states would correspond closely to those described in detail above, where the residue is the resist and the residue states correspond to whether the resist is or is not cleared.

What is claimed is:

1. An inspection method for determining quality states of a wafer comprising the steps of:
    a) calculating first spectral signatures from a first set of measurement sites on one or more training wafers, wherein each of said measurement sites is known to be one of two or more different states indicative of quality in the processing of a wafer;
    b) correlating said first spectral signatures to the respective states;
    c) calculating second spectral signatures from a second set of measurement sites on a wafer of unknown quality state to be determined; and
    d) determining the two or more states of at least one measurement site in said second set of measurement sites on the wafer based on said second spectral signatures obtained in said step (c).

2. A method according to claim 1, wherein said two or more states correspond to amounts of residue present on the wafer.

3. A method according to claim 2, wherein said two or more states consists of first and second states, wherein said first state corresponds to the presence of residue and said second state corresponds to the absence of residue.

4. A method according to claim 1, wherein said step a) includes the step of inspecting said training wafer to determine the state for each of said first set of measurement sites.

5. A method according to claim 1, wherein said first spectral signatures are derived from first reflected spectra measured at said first set of measurements sites, and said second spectral signatures are derived from second reflected spectra measured at said second set of measurement sites.

6. A method according to claim 5, wherein said first and second reflected spectra are optical spectra.

7. A method according to claim 6, wherein said optical spectra correspond to reflected intensity as a function of wavelength.

8. A method according to claim 6, wherein said optical spectra correspond to reflected intensity as a function of angle.

9. A method according to claim 6, wherein said optical spectra correspond to one or more ellipsometric parameters as a function of wavelength.

10. A method according to claim 6, wherein said optical spectra correspond to one or more ellipsometric parameters as a function of angle.

11. A method according to claim 6, wherein said first and second spectral signatures are either scalars or vectors.

12. A method according to claim 5, wherein calculating said first and second spectral signatures includes at least one of the steps of:
   i) calculating an extremum value of one of said first measured spectra;
   ii) calculating a percentile of one of said first measured spectra;
   iii) fitting a curve to one of said first measured spectra;
   iv) calculating an extremum value of one of said second measured spectra;
   v) calculating a percentile of one of said second measured spectra; and
   vi) fitting a curve to one of said second measured spectra.

13. A method according to claim 1, wherein said step b) further includes the steps of determining a spectral signature threshold quantity from said first spectral signatures.

14. A method according to claim 13, wherein said step d) further includes the step of comparing said second signatures to said spectral signature threshold quantity.

15. A method according to claim 14, wherein said spectral signature threshold quantity is a scalar or a vector.

16. A method according to claim 1, wherein each said spectral signature quantity is a vector, and wherein said step b) includes the steps of:
   i) deriving N coordinate values for each vector;
   ii) plot ting the vector in N-space as a plurality; and
   iii) selecting a curve or surface in the N-space representing the spectral signature threshold as the curve or surface that best divides the points into regions indicative of states.

17. A method according to claim 16, wherein the curve in N-space is selected based on optimization of the probabilities of obtaining a false determination of two or more states.

18. A method according to claim 17, wherein the optimization gives preference to the false determination of one state over another.

19. A method according to claim 1, further including in said step d) the step of determining whether a state of at least one of the second set of measurement sites is ambiguous.

20. A method according to claim 19, further including the step of determining the likelihood that the ambiguous state does not exist on the wafer.

21. A method according to claim 19, further including the step of determining the likelihood that the ambiguous state does exist on the wafer.

22. An apparatus for inspecting a wafer having an upper surface to determine a quality state of the wafer, comprising:
   a) a stage for positioning the wafer with respect to the measurement unit;
   b) an measurement unit for measuring reflected spectra from the wafer arranged adjacent the wafer upper surface;
   c) a control system electrically connected to said stage and said measurement unit, wherein said control system is programmed to perform the steps of:
      i) calculating first spectral signatures from a first set of measurement sites on one or more training wafers, wherein each of said measurement sites is known to be one of two or more states indicative of quality in the processing of a wafer;
      ii) correlating said spectral signatures to said two or more states;
      iii) calculating second spectral signatures from a second set of measurement sites on a wafer of unknown quality state to be determined; and
      vi) determining the states on the wafer based on said second spectral signatures obtained in said step iii).

23. An apparatus according to claim 22, wherein said two or more states are residue states.

24. A set of instructions for a computer embodied in a computer-readable medium for performing the steps of:
   a) calculating first spectral signatures from a first set of measurement sites on one or more training wafers, wherein each of said measurement sites is known to be one of two or more states;
   b) correlating said spectral signatures to said two or more states;
   c) calculating second spectral signatures from a second set of measurement sites on a wafer of unknown states to be determined; and
   d) determining the states on the wafer based on said second spectral signatures obtained in said step d).

* * * * *